(12) United States Patent
Alexandre et al.

(10) Patent No.: US 7,056,300 B2
(45) Date of Patent: Jun. 6, 2006

(54) NEEDLELESS SYRINGE FOR INJECTING A LIQUID CONTAINED IN A PREFILLED AMPULE

(75) Inventors: Patrick Alexandre, Gray (FR); Bernard Brouquieres, Toulon (FR); Xavière Castano, Dijon (FR); Philippe Gautier, Le Plessis Pate (FR)

(73) Assignee: Crossject, Paris (FR)

( * ) Notice: Subject to any disclaimer, the term of this patent is extended or adjusted under 35 U.S.C. 154(b) by 550 days.

(21) Appl. No.: 10/169,997

(22) PCT Filed: Jan. 26, 2001

(86) PCT No.: PCT/FR01/00250

§ 371 (c)(1),
(2), (4) Date: Jul. 12, 2002

(87) PCT Pub. No.: WO01/58512

PCT Pub. Date: Aug. 16, 2001

(65) Prior Publication Data

US 2003/0050596 A1    Mar. 13, 2003

(30) Foreign Application Priority Data

Feb. 11, 2000  (FR) .................................. 00 01721

(51) Int. Cl.
*A61M 5/30* (2006.01)

(52) U.S. Cl. .............................. 604/69; 604/70; 604/68
(58) Field of Classification Search ............ 604/68–70, 604/140, 500.82
See application file for complete search history.

(56) References Cited

U.S. PATENT DOCUMENTS

| 3,788,315 A | * | 1/1974 | Laurens .................. 604/70 |
| 4,668,223 A |   | 5/1987 | Grotenhuis |
| 5,730,723 A | * | 3/1998 | Castellano et al. ......... 604/68 |
| 6,004,287 A |   | 12/1999 | Loomis et al. |

FOREIGN PATENT DOCUMENTS

| EP | 0 888 791 A1 | 1/1999 |
| FR | 2 775 603 | 9/1999 |
| WO | WO 00/48654 | 8/2000 |

* cited by examiner

*Primary Examiner*—Nicholas D. Lucchesi
*Assistant Examiner*—Aamer Syed Ahmed
(74) *Attorney, Agent, or Firm*—Oliff & Berridge, PLC

(57) ABSTRACT

A needleless syringe comprises a reservoir sealed with mobile closure elements enclosed the liquid, the reservoir being initially isolated from the injection system which is so designed that it comprises at least two peripheral injection conduits located outside a receptacle comprising a blind bore which receives the downstream closure element such that the inlets of the conduits are cleared.

14 Claims, 3 Drawing Sheets

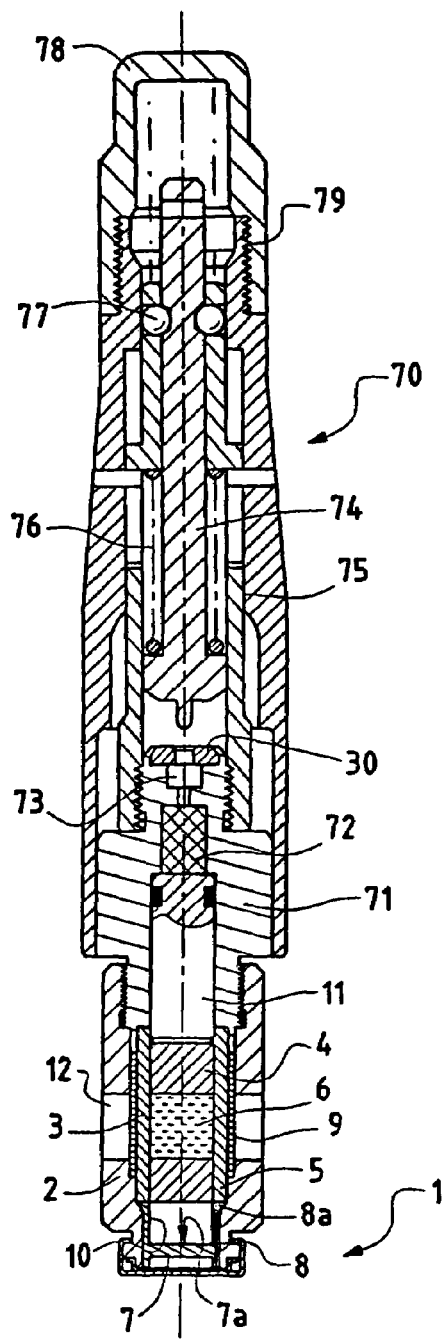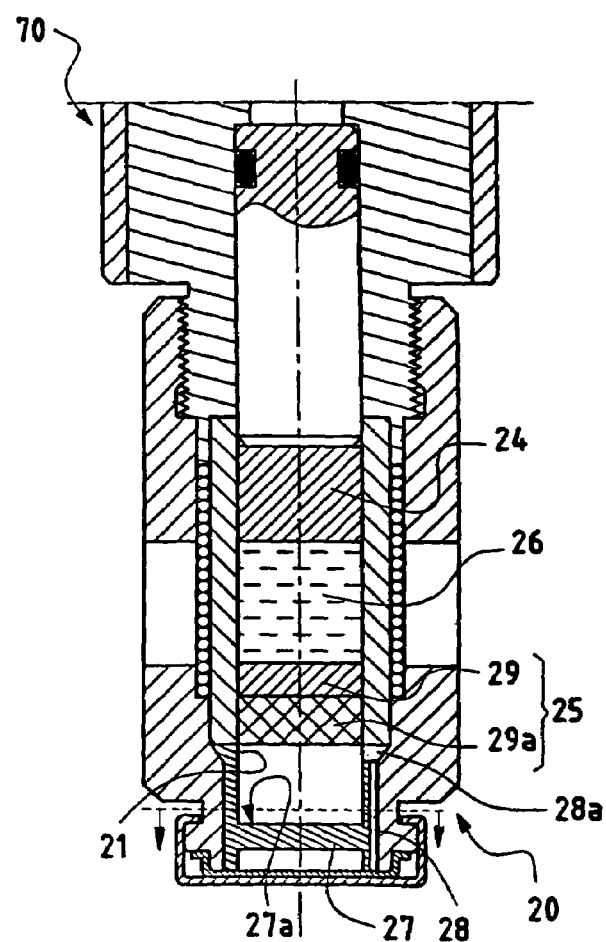
FIG.1
FIG.2

NEEDLELESS SYRINGE FOR INJECTING A LIQUID CONTAINED IN A PREFILLED AMPULE

BACKGROUND

The present invention concerns the field of prefilled and disposable needleless syringes; such syringes are used for intradermal, subcutaneous and intramuscular injections of liquid active principle intended for therapeutic use in human or veterinary medicine.

A first imperative for prefilled syringes is that of the compatibility in the long term, generally three years, between the liquid active principle and the reservoir which contains it. Another imperative, associated with the prefilling method, is that of having a transparent reservoir in order to be able to carry out the regulatory checks of correct filling of the reservoir before it is fitted in the syringe. These imperatives result in the production of a reservoir which is substantially transparent and made of a material which is compatible with the active principle for the desired length of time: this material is generally glass for pharmaceutical use: glass type I or II.

The initial phase of the injection is critical for the penetration, into the skin, of the jet or jets of liquid, depending on whether the syringe has one or more injection conduits. The latter configuration being favorable for reducing pain. The final bioavailability depends on the correct implementation of this initial phase, it assumes a rapid acceleration of the liquid in the injection conduits without the multiple jolts of the jets when there is too great a pressure surge to achieve this rapid acceleration.

The prior art does not disclose syringes, with several injection conduits, meeting all of these requirements.

The patent FR 2 775 603 describes a needleless syringe with a prefilled ampule closed at its upstream end by a displaceable obturator and at its downstream end by a multi-hole injector having a central filling orifice closed by a stopper after the ampule has been filed.

The U.S. Pat. No. 4,668,223 describes a syringe with a prefilled ampule which is closed at each of its ends by a displaceable obturator, the upstream end of the ampule receives a guide piece for a plunger rod and the downstream end receives a part forming a receptacle in which the downstream obturator is to be housed.

The U.S. Pat. No. 4,941,880 describes a syringe which is very complex from several points of view. First, it is a syringe with a pneumatic drive, intended to be used several times by changing the ampule containing the active principle. This ampule containing the active principle comprises two juxtaposed parts. An upstream part, for long-term storage of the active principle: this is a glass tube closed at its two ends by obturators and placed in a polycarbonate tube; this arrangement ensures the compatibility and allows the filling to be checked. Before use, the operator transfers the active principle into the downstream part of the ampule, which has the role of intermediate reservoir, by pushing a plunger which displaces the liquid and the downstream obturator; this downstream part of the reservoir is made of polycarbonate and has a thick wall, it will withstand the operating pressure generated by the drive device. The operator places the ampule, thus prepared for injection, into the injection mechanism; upstream of an injection device comprising a single injection conduit which will be supplied via a bypass placed at the downstream end of the intermediate injection reservoir. This arrangement solves the problems of resistance of the reservoir and to a certain extent can reduce the initial jolts of the injection, but with considerable pressure losses in a tortuous injection system for supplying a single injection conduit. The complexity of the device both in terms of its production and its use is self-evident.

SUMMARY

The present invention aims to solve all of these problems by means of a device which is as simple as possible, is disposable after injection, and can be used not only by specialized personnel but also by an ordinary patient.

The present invention concerns a needleless syringe comprising a substantially cylindrical reservoir closed off by a displaceable upstream obturator, a displaceable downstream obturator and enclosing a liquid active principle, the reservoir being initially isolated from an injection system integral with a body, said syringe comprising a drive means for displacing the assembly of upstream obturator, liquid and downstream obturator, is characterized in that the injection system comprises at least two peripheral injection conduits which are situated outside a receptacle for the downstream obturator, the free height of the blind bore of the receptacle permitting clearance of the inlets of the peripheral conduits when this downstream obturator is in contact with the bottom of the receptacle.

In this invention, liquid active principle, or medicament, is to be understood principally as meaning a more or less viscous liquid, or a mixture of liquids, or a gel. The active principle can be a solid dissolved in a suitable solvent for injection. The active principle can be a solid in pulverulent form in more or less concentrated suspension in a suitable liquid. The granulometry of the solid active principle must be adapted, as must the form of the conduit, to avoid blockages.

The substantially cylindrical reservoir is made of glass type I or type II; but it can be made of any other material that is transparent and compatible with the active principle.

The drive means which will act on the upstream obturator can be a mechanical drive: release of a compressed spring, or of the pneumatic type: release of compressed gas, or pyrotechnic: release of combustion gas.

The syringe functions in the following way: the drive means will act on the upstream obturator and displace the assembly of upstream obturator, liquid and downstream obturator because the liquid is incompressible. The downstream obturator is displaced and lodges in the blind bore of the receptacle until contact is made with the bottom of said receptacle. The height of this bore is such that when the downstream obturator is in contact with the bottom of the receptacle, the inlets of the injection conduits, on the periphery of the receptacle, are freed; the liquid is driven back there and is injected by the movement of the upstream obturator, which continues until the reservoir is emptied: the upstream obturator is then in contact with the downstream obturator.

The needleless syringe is preferably such that the reservoir of liquid active principle is housed in the body on which the injection system is fixed.

According to one variant, the receptacle in which the downstream obturator lodges is a part of the body of the syringe.

The receptacle for the downstream obturator advantageously comprises at least one means for absorbing the impact of the downstream obturator before it comes to a stop in the bottom of the receptacle. This shock absorption, which prevents rebounding of the obturator, has the purpose of preventing injection jolts at the start of operation.

According to a first variant, the downstream obturator comprises, on its face directed toward the receptacle, a recess with a shape matching that of a stud which is integral with the bottom of the receptacle. During its displacement, the downstream obturator will engage on the stud via this recess. This engagement absorbs the energy of the impact of the obturator on the bottom of the receptacle. Moreover, this engagement is rendered irreversible, for example by a flange or notches disposed around the stud.

According to another variant, the downstream obturator can lodge in a receptacle of very slightly truncated shape with a large cross section at the entrance to the receptacle and a smaller cross section at the bottom. The deformation of the obturator for lodging in this receptacle absorbs the impact.

According to another variant, the downstream obturator comprises a compressible part. The downstream obturator lodges in the bore of the receptacle by crushing this compressible part: the depth of the bore is less than the height of the obturator before its deformation. It is the crushing of this deformable part which absorbs the impact of the downstream obturator.

According to a first embodiment, the drive means acts directly on the upstream obturator.

According to another embodiment, the drive means acts on the upstream obturator by way of a plunger. This variant is of interest when the drive means is a generator of the pneumatic type or of the pyrotechnic type. By then using a stepped plunger, instead of a single plunger, it is possible to effect a first phase at low pressure and low speed in order to displace the assembly of upstream obturator, liquid and downstream obturator, and to engage the downstream obturator without shock in the receptacle, then a second phase at high pressure for injection at high speed.

The drive means is preferably a pyrotechnic gas generator. Such a device is compact, powerful and in particular very reliable: the storage life of this type of generator is much longer than the period of conservation of the active principle.

The reservoir and the body of the syringe advantageously form a single unit which is compatible with the active principle for a long period of time and is resistant to high pressures during functioning.

According to another embodiment, the reservoir is shrink-fitted into the body by way of an intermediate material upon assembly of the body of the syringe with the reservoir onto the drive means.

The body of the syringe is advantageously made of a transparent material making it possible to view the reservoir of active principle up to the moment of injection.

However, the body comprises at least one window for viewing the content of the reservoir when the material of the syringe body is not transparent.

The plunger acting on the upstream obturator advantageously serves as an indicator of the functioning of the syringe by appearing in the transparent part or the window of the body of the syringe. The upstream obturator can also fulfill this function.

The needleless syringe with several injection conduits in the different embodiments of the invention solves the problems posed. The long-term compatibility between the liquid active principle and the reservoir containing it, by the choice of the shape and materials of the reservoir. The stability of the reservoir with respect to the high operating pressure, by the different types of assembly of the reservoir in the body. Injection without jolts at the start of the phase of acceleration of the liquid, by the functioning of the device and the absorption of the impact.

The air initially trapped in very small quantity in the injection conduits does not introduce any adverse effect. Likewise, the active principle which remains in the conduits at the end of injection entails a very negligible loss of active principle, which can even be compensated for at the time of prefilling.

The present invention has the advantage of making it possible to separate two parts of the device. A part which will be called the pharmaceutical part comprising the body and the reservoir with the displaceable upstream and downstream obturators: this subassembly will be able to be processed under the conditions applying in the pharmaceutical industry, in particular as regards sterilization and asepsis. This subassembly will be integrated with the rest of the syringe whose elements have been joined together, this assembling being done under less stringent conditions than those associated with the pharmaceutical industry.

When the downstream obturator is lodged irreversibly in the receptacle, the syringe becomes very difficult to reuse. This arrangement therefore also has the advantage of preventing reuse of said syringe for purposes other than the initial therapeutic use.

Finally, this configuration has the advantage of preventing possible leaking of liquid via the injection conduits before the injection is performed. This is because the device is frequently shaken (this is even recommended) in order to examine the turbidity of the liquid or to homogenize the mixture when the liquid comprises particles in suspension. The fact that, before injection, the active principle is isolated from the conduits affords ultimate protection against this risk of loss.

BRIEF DESCRIPTION OF THE DRAWINGS

The invention is set out in detail below with the aid of figures representing different specific embodiments of the invention.

FIG. 1 shows a longitudinal section through a syringe according to a first embodiment.

FIG. 2 shows the partial view of the downstream end of a syringe in which the downstream obturator has a compressible part.

DETAILED DESCRIPTION OF THE EMBODIMENTS

Figure 3:
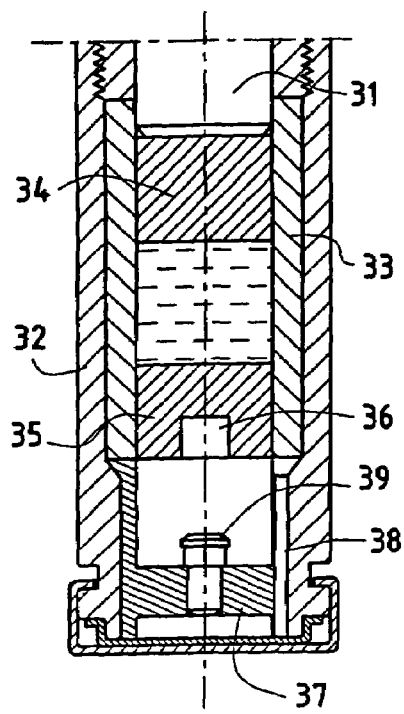
FIGS. 3 and 4 show a partial view of the downstream end of a syringe according to another variant, respectively before and after functioning, and in this variant the downstream obturator comprises a recess.

FIG. 1 shows, in longitudinal section, a syringe according to the invention, it is shown vertically, the injection system directed downward.

The syringe 1 comprises a body 2 which houses a reservoir 3 containing the liquid active principle 6. Placed at the downstream end of the body 2 there is a receptacle 7 comprising, for example, three injection conduits, such as the conduit 8. The injection system is covered by an external protection in order to ensure asepsis of the syringe: this protection comprises an elastomeric membrane applied on the outer face of the injector via a fine metal protective seal, crimped about this end of the syringe. This protection will be removed before the injection. At its opposite end, the body 2 of the syringe is fixed to a drive means 70 which, in this example, is a pyrotechnic gas generator, which will be described below.

The body 2 of the syringe comprises two diametrically opposite windows for viewing the active principle contained in the reservoir 3: these are simply two oblong openings 12 in the body. Arranged downstream of the body 2 of the syringe, and engaged in a bore of suitable shape, there is a cylindro-conical receptacle 7, which will be described below. A reservoir 3 made of glass is positioned bearing on this receptacle 7 and centered downstream of the body 2; this reservoir is a tube surrounded by a transparent intermediate material 9. Upstream, the body 2 of the syringe receives the body 71 of the drive means which is centered about the other end of the reservoir, the annular centering crown bears on the intermediate material 9 and thus shrink-fits the reservoir 3 in the body 2 at the moment of assembly of the drive means onto the body 2 of the syringe. This shrink-fitting increases the resistance of the tube when it is subjected to the operating pressure. The reservoir 3 is essentially a tube which is closed off at its two ends by displaceable upstream 4 and downstream 5 obturators; these obturators are preferably plunger stoppers commonly used in syringes: these are parts which are obtained by molding of elastomers which are compatible with the active principle over a long period of time: each part incorporates the functions of plunger and leaktightness via flanges or lips (not detailed in the figures). The elastomers normally used for the production of these parts are, for example, chlorobutyl or bromobutyl, whose Shore hardness is set at about 45 and about 70. These parts can be given surface treatments, in particular to facilitate their displacements in the tubular reservoir. When it is free, the plunger stopper has a diameter greater by about 10 percent than the internal diameter of the tube which is going to receive it, the height of the plunger stopper is about 0.5 to 0.8 times this diameter. When the plunger stopper is engaged in the tube, because of the deformations its height is equal to about 0.6 times to about 1.0 times the internal diameter of the reservoir.

In this example, the receptacle 7 is a part with a cylindro-conical external shape which comprises a central bore 10 in which the downstream obturator 5 will lodge. On its periphery, the receptacle comprises three injection conduits, only one of which, labeled 8, can be seen in this cross section. The diameter of the bore is equal to that of the reservoir. The free height of the blind bore 10 of the receptacle 7 is equal to that of the downstream obturator 5 mounted in the reservoir 3. When the downstream obturator 5 has reached the bottom 7a of the receptacle, the inlet 8a (toward reservoir 3) of the injection conduits 8 is brought into communication with the liquid 6; the liquid flows with a speed corresponding to the pressure transmitted by the upstream obturator 4.

In this embodiment, the drive means acts on the upstream obturator by way of a plunger 11 with an effective cross section equal to that of the upstream obturator 4, this plunger 11 is in contact with the upstream obturator 4, there is therefore no shock or pressure surge effect at the start of functioning. By virtue of its leaktight system, this plunger 11 prevents the gases produced by the combustion of the charge 72 from coming into contact with the upstream obturator and thus prevents possible damage to the latter and escape of gases toward the active principle contained in the reservoir. This plunger 11, given a suitable colour, can also serve as an indicator of functioning by appearing in the viewing windows of the body 2 of the syringe.

We will now describe the main elements of the pyrotechnic generator 70. It comprises, in the body 71 above the plunger, a pyrotechnic charge 72 whose combustion is initiated by a primer 80 impacted by a striker 74. The primer 73 is housed in a primer holder. In the initial position, the striker 74 is retained in the striker guide 75, made integral by screwing to the body 71, by means of at least one ball, such as the ball 77, partially engaged in a groove of the striker. The striker device comprises a push button 78 with a groove 79 and an internal spring 76.

The push button 78 slides on the outside of the striker guide 75 and it is held by stubs which move in lateral grooves. This push button 78 is in this case the trigger member.

In order to initiate the combustion of the pyrotechnic charge 72, it is of course possible, without departing from the scope of the invention, to use initiation devices other than the striker device described here. Without going into details and without wishing to be exhaustive, we will cite, as examples, initiation devices with an electric battery or piezoelectric initiation devices.

If appropriate, the pyrotechnic gas generator can be replaced by a gas generator formed by a reservoir of compressed gas closed by a valve which can open quickly. The triggering member will open said valve, the compressed gases of the reservoir will expand and act on the thrust means.

After removing the asepsis stopper, and having placed the downstream face of the injector on the skin of the subject who is to be treated, the operator presses with his thumb on the push button 78 which is driven down and compresses the spring 76. The push button is displaced until the groove 78 arrives level with the groove of the striker 74, the balls, such as the ball 77, retaining the striker 74 move into the groove 79 and release the striker, which will violently impact the primer 73, whose initiation fires the pyrotechnic charge 72. The striker 74 bearing on the primer holder 80 ensures that the primer is held in place and ensures leaktightness: the gases of combustion do not ascend toward the push button.

The combustion of the pyrotechnic charge will produce gases which act on the plunger 11.

Figure 6:
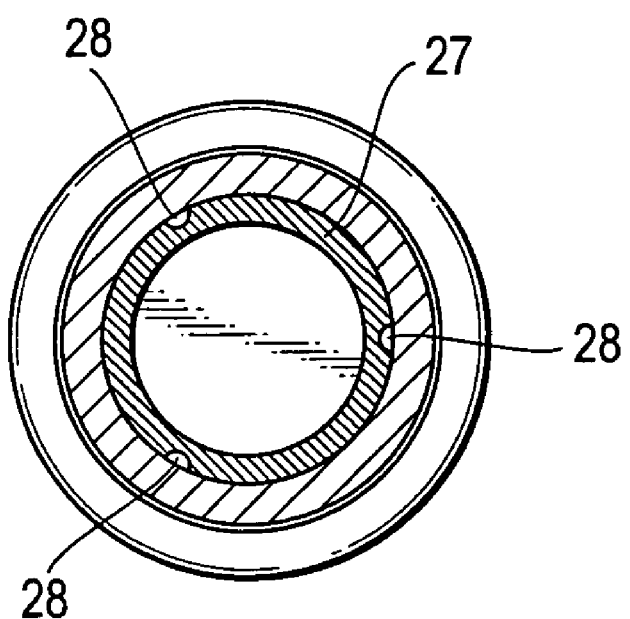
FIG. 6 shows a cross-sectional view indicated in FIG. 2.

FIG. 2 shows the partial view of another embodiment 20 of the invention in which the downstream obturator 25 is partially compressible. FIG. 6 is a cross-sectional view indicated in FIG. 2, showing three injection conduits 28 on the periphery of the receptacle 27. Before functioning, this obturator has a height or thickness greater than the height of the blind bore 21 of the receptacle 27. As before, the drive means displaces the assembly of upstream obturator 24, liquid 26 and downstream obturator 25; the downstream obturator lodges in the blind bore 21 of the receptacle, then comes into contact with the bottom 27a and, under the effect of the pressure, the compressible part crushes, frees the inlets 28a of the injection conduits 28 and permits passage of the liquid. The deformation by partial compression of the downstream obturator 25 in the blind bore of the receptacle absorbs the shock due to the arrest of the downstream obturator and prevents ejection of the liquid in multiple spurts. The downstream obturator 25 is formed, for example, by two layers of different materials: toward the reservoir, a layer of deformable but incompressible elastomer 29, compatible with the active principle, then below this a layer of a very compressible material 29a which will crush when the downstream obturator engages at the bottom of the receptacle.

In one variant, the downstream obturator is made of the same elastomer compatible with the active principle but comprises on its lower part, coming into contact with the bottom of the receptacle, at least one cavity which will be closed by the deformation of the elastomer upon engagement of the downstream obturator in the receptacle. This deformation absorbs the impact of the obturator and also reduces the volume occupied by the obturator.

FIG. 3 shows, in a partial view, another embodiment of the invention which differs from the preceding ones in terms of the particular shape of the downstream obturator and the fitting of the reservoir in the body of the syringe.

The body 32 of the syringe is made of a material which is transparent and sufficiently thick to withstand high operating pressures. A cylindro-conical receptacle 37 is engaged in the downstream end of the body 32. The reservoir 33 containing the liquid active principle and closed off by the upstream 34 and downstream 35 obturators is housed in the body 32. The body 32 serves as a reinforcement for the reservoir 33 at the moment of the injection.

Another particular feature of this example is the recess 36 on the downstream face of the displaceable obturator 35 and the stud 39 fixed in the bottom of the receptacle. The recess 36 and the stud 39 have shapes which permit their engagement when the downstream obturator 35 is displaced under the effect of the pressure transmitted by the plunger 31. This engagement absorbs the energy and cushions the impact of the obturator 35 on the bottom of the receptacle 37: there is no rebound of the downstream obturator 35, which remains engaged on the stud 39.

The shock absorption of the downstream obturator in the receptacle can also be achieved by means of a receptacle of slightly truncated shape in which the downstream obturator will lodge and deform.

The shock absorption can also be achieved pneumatically by at least one calibrated vent hole which controls the flow rate of air driven by the downstream obturator upon its displacement in the receptacle.

Figure 4:
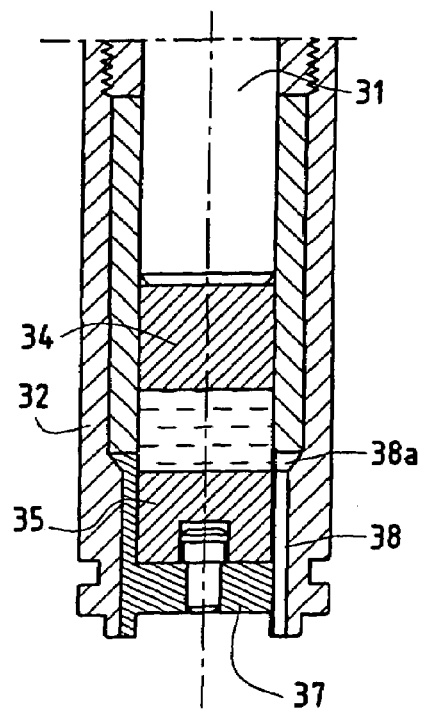

FIG. 4 shows, in a partial view, the position of the downstream 35 and upstream 34 obturators during the injection. The downstream obturator 35 is in the blind bore of the receptacle 37, it is engaged via its recess 36 on the stud 39 fixed on the bottom of the receptacle: this engagement is rendered irreversible by a flange surrounding the stud 39. The upstream obturator 34, pushed by the plunger 31, drives the liquid. This FIG. 4 illustrates clearly an injection in progress: the obturator 35 is bearing on the bottom of the receptacle 37 and it frees the inlets 38a of the injection conduits 38 and does so until the upstream obturator 34 has terminated its travel and come to bear on the downstream obturator 35.

Figure 5:
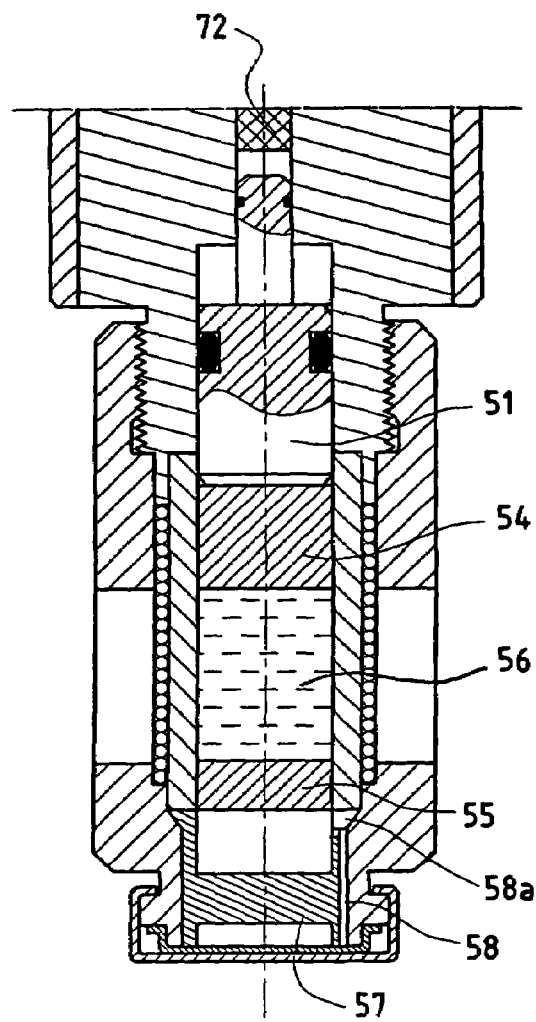
FIG. 5 shows a variant with a stepped plunger for displacing the upstream and downstream obturators.

FIG. 5 shows another embodiment of the invention which differs from the example in FIG. 2 in terms of the use of a stepped plunger 51. Toward the gas generator, the plunger 51 comprises a head of small cross section which will transmit a moderate force, at the start of functioning, for setting into motion and accelerating the assembly of upstream obturator 54, liquid 56 and downstream obturator 55. The lengths of displacement are chosen in such a way that when the head of small cross section is freed, more precisely when the upper seal of the plunger 51 ceases to be effective, the downstream obturator 55 is housed entirely in the receptacle 57, the gases of the generator will then act on the large cross section of the plunger 51 subjecting the liquid 56 to a high pressure and, as it is then brought into communication with the openings 58a of the injection conduits 58, the liquid 56 will be injected at high speed, which is favorable for penetrating the skin and for good bioavailability of the active principle.

The invention claimed is:

1. A needleless syringe, comprising:
    a body housing a cylindrical reservoir closed off by a displaceable upstream obturator and a displaceable downstream obturator enclosing an active principle; and
    a downstream receptacle with at least two peripheral injection conduits which are placed around and outside a sidewall of said receptacle, said receptacle comprising a blind bore whose free height permits clearance of the inlets of the peripheral conduits when the downstream obturator is brought into contact with the bottom of said receptacle by a drive means displacing the assembly of the upstream obturator, the active principle and the downstream obturator,
    wherein the receptacle comprises a means for shock absorption of the downstream obturator before it comes to a stop in the receptacle.

2. The needleless syringe as claimed in claim 1, further comprising a stud provided at the downstream obturator is received by a recess.

3. The needleless syringe as claimed in claim 1, wherein the downstream obturator is deformable.

4. The needleless syringe as claimed in claim 3, wherein the receptacle is smaller than the downstream obturator before its deformation.

5. The needleless syringe as claimed in claim 1, wherein the drive means acts directly on the upstream obturator.

6. The needleless syringe as claimed in claim 1, wherein the drive means acts on the upstream obturator by way of a plunger.

7. The needleless syringe as claimed in claim 6, wherein the plunger is a stepped plunger in order to effect a first phase at low pressure and low speed to displace the assembly of upstream obturator, liquid and downstream obturator and engage the downstream obturator without shock in the receptacle, then a second phase at high pressure for injection at high speed.

8. The needleless syringe as claimed in claim 7, wherein, on the gas generator side, the stepped plunger comprises a head of small cross section for producing a moderate force to move the assembly of upstream obturator, liquid and downstream obturator, the length of displacement being such that when the head of small cross section is cleared, the downstream obturator is housed entirely in the receptacle and the gases from the generator will then act on the large cross section of the plunger: the liquid is subjected to a high pressure.

9. The needleless syringe as claimed in claim 1, wherein the drive means is a pyrotechnic gas generator.

10. The needleless syringe as claimed in claim 1, wherein the reservoir and the body form a single unit.

11. The needleless syringe as claimed in claim 1, wherein the reservoir is shrink-fitted into the body via an intermediate material upon assembly onto the drive means.

12. The needleless syringe as claimed in claim 1, wherein the body is transparent.

13. The needleless syringe as claimed in claim 1, wherein the body comprises at least one window for viewing the content of the reservoir.

14. The needleless syringe as claimed in claim 1, wherein the assembly of the upstream obturator, the active principle and the downstream obturator are displaced together when the drive means is actuated.

* * * * *